US006174537B1

(12) United States Patent
Khan

(10) Patent No.: US 6,174,537 B1
(45) Date of Patent: Jan. 16, 2001

(54) CATHETER FLUSH SOLUTION AND METHOD FOR ITS USE

(75) Inventor: Mohammad A. Khan, Sandy, UT (US)

(73) Assignee: Becton, Dickinson and Company, Franklin Lakes, NJ (US)

( * ) Notice: Under 35 U.S.C. 154(b), the term of this patent shall be extended for 0 days.

(21) Appl. No.: 09/160,745

(22) Filed: Sep. 25, 1998

(51) Int. Cl.$^7$ ................................................. A01N 25/02
(52) U.S. Cl. ........................ 424/405; 424/409; 514/635
(58) Field of Search ................................. 424/405, 422, 424/423, 409; 514/635; 128/200.14; 604/27, 48

(56) References Cited

U.S. PATENT DOCUMENTS

| | | | |
|---|---|---|---|
| Re. 32,300 | * 12/1986 | Gorman et al. | 514/635 |
| 3,183,230 | * 5/1965 | Shapiro | 424/54 |
| 5,362,754 | 11/1994 | Raad et al. | 514/566 |
| 5,449,658 | * 9/1995 | Unhoch et al. | 504/151 |
| 5,688,516 | 11/1997 | Raad et al. | 424/409 |
| 5,772,640 | 6/1998 | Modak et al. | 604/265 |
| 5,783,091 | * 7/1998 | Werle et al. | 210/755 |

OTHER PUBLICATIONS

Inhibitory Effect of Disodium EDTA upon the Growth of *Staphylococcus epidermidis* In Vitro: Relation to Infection Prophylaxis of Hickman Catheters, Antimicrobial Agents and Chemotherapy, Nov. 1988, p. 1627–1631, vol. 32, No. 11.

Stefania Zanetti, Pier Luigi Fiori, Antonio Pinna, Stefania Usai, Francesco Carta and Giovanni Fadda, Susceptibility of *Acanthamoeba castellanii* to Contact Lens Disinfecting Solutions, Antimicrobial Agents and Chemotherapy, Jul. 1995, vol. 39, No. 7, pp. 1596–1598.

R. Christiansen, K. H. Palmork, Distribution and Elimatin of [14C] in Saithe (Pollachius Virens L.) After Application of a Single Dose of [14C] Polyhexamethylene Hydrochloride-biguanide,. Bull. Environ. Contam. Toxicol. (1996) 56:121–128.

Sales Literature for "BAQUACIL", ICI Amerias Inc., pp. 1–22, 1986.

Article on COSMOCIL CQ, Polyhexamethylene Biguanide Hydrochloride Solution, ICI Amerias Inc., 100–6, 4/86 200, pp. 1–6.

Abstracts, APS Pacific Division, vol. 85, No. 9, 1995.

Jennifer L. Root, O. Ross McIntyre, Nicholas J. Jacobs and Charles P. Daghlian, Article entitled: Inhibitory Effect of Disodium EDTA Upon the Growth of *Staphylococcus epdermidis* in Vitro: Relation to Infection Prophylaxis of Hickman Catheters, Antimcirobial Agents and Chemotherapy, Nov. 1988, pp. 1627–1631.

James Keeven, MS, Stan Wrobel, PhD, Marta Portoles, PhD, B.T. DeCicco, PhD, Article entitled: Evaluating the Preservative Effectiveness of RGP Lens Care Solutions, the CLAO Jounal, Oct. 1995, vol. 21. No. 4, pp. 235–241.

Milks: Practical Veterinary Pharmacology–p. 118, 1949.*

* cited by examiner

*Primary Examiner*—Neil S. Levy
(74) *Attorney, Agent, or Firm*—Eric M. Lee, Esq.

(57) ABSTRACT

A solution of the present invention useful for flushing an intravascular catheter includes a pharmacologically acceptable sodium salt, a pharmacologically acceptable calcium salt, a pharmacologically acceptable potassium salt and about one milligram per milliliter polyhexamethylene biguanide hydrochloride in an aqueous admixture. Additionally, the solution of the invention may also contain a pharmacologically acceptable salt of lactic acid.

10 Claims, No Drawings

CATHETER FLUSH SOLUTION AND METHOD FOR ITS USE

FIELD OF INVENTION

The present invention is generally related to intravascular catheters and more particularly to a solution useful for maintaining the patency of a long-term indwelling intravascular catheter and a method for its use.

BACKGROUND

Intravascular catheters are among the most commonly used medical devices. Such catheters are routinely placed into a patient's vascular system for many procedures and often are left in place for extended periods. Since an intravascular catheter is a direct path from the outside environment to the patient's bloodstream, the catheter's presence presents a substantial and continuous potential for introduction of microorganisms into the patient's bloodstream. Practitioners have developed many protocols related to placement, use, attachment and detachment of fluid handling devices and other procedures related to catheters. The goal of almost all of these procedures is to avoid introduction of a microorganism into the patient's bloodstream. When a medicament is introduced into a patient through a catheter, the practitioner commonly follows the introduction with a flush solution that may include an anticoagulant such as heparin. The purpose of the flush solution is to move the medicament out of the catheter so that the entire dosage is delivered, and to leave a residual fill in the catheter so that the patient's blood does not back up in the catheter and possibly form a clot that would occlude the bore of the catheter. Thus, when the catheter is subsequently needed again, the properly flushed catheter is likely fully patent and ready for the next usage.

In 1988, Root, et al., published a study that reported on the effect of disodium ethylene diamine tetra acetic acid (EDTA), a compound well known for its chelating properties in vivo and widely used as an anticoagulant in vitro. The authors compared EDTA, heparin and vancomycin/heparin for effectiveness upon the growth of S. epidermis in vitro and its relation to infection prophylaxis of Hickman catheters in their report in Antimicrob. Agents Chemother., 32:1627–1631, 1988. Recently, Raad, et al. in U.S. Pat. No. 5,363,754 disclosed that pharmaceutical compositions of a mixture of minocycline and EDTA were useful in maintaining the patency of a catheter port. More recently, Raad, et al. in U.S. Pat. No. 5,688,516 further disclosed that effective catheter flush solutions could be prepared with non-glycopeptide antimicrobial agents other than vancomycin and a second agent selected form the group consisting of: (a) an anticoagulant, (b) an antithrombotic agent and (c) a chelating agent selected from a group of chelating agents. Raad, et al. teaches that since many antibiotic agents are not particularly stable at ambient conditions in aqueous solutions, that the disclosed compositions are stable and effective for about one month when stored under refrigerated conditions and that the solution should be brought to room temperature before administration to a patient. Alternatively, Raad, et al. teaches a kit including three compartments, the compartments containing the antimicrobial agent, the chelating, anticoagulant or antithrombotic agent and a diluent such as saline, Ringers solution or water so that the practitioner could mix the components prior to administration to the patient, thereby avoiding the reported stability problems.

While the disclosures of Raad, et al. teach a series of antimicrobial agents with a variety of other compounds, given the tendency of microorganisms to develop resistance to many antibiotic agents and the sensitivity to many people to certain antibiotics and other compounds, there still is a need for a catheter flush solution that does not include an antibiotic, is stable under ambient storage conditions and contains only materials with little likelihood of inducing an allergic response in a sensitive patient. Such a solution is disclosed hereinbelow.

SUMMARY

A solution of the present invention useful for flushing an intravascular catheter includes a pharmacologically acceptable sodium salt, a pharmacologically acceptable calcium salt, a pharmacologically acceptable potassium salt and about one milligram per milliliter polyhexamethylene biguanide hydrochloride in an aqueous admixture. Additionally, the solution of the invention may also contain a pharmacologically acceptable salt of lactic acid.

The catheter flush solution of the invention, when compared under in vitro simulated use conditions to a known catheter flush solution composed of minocycline and ethylenediaamine tetra acetic acid (M-EDTA), suprisingly showed similar results in activity against microorganisms in established biofilms. Additionally, unlike the M-EDTA, which is stable for about one month under refrigeration, the catheter flush solution of the invention retains full activity even after autoclave sterilization or ultra filtration. The catheter flush solution of the invention is simple to prepare, is thermally stable and has acceptable toxicity properties consistent with its intended use.

DETAILED DESCRIPTION

While this invention is satisfied by embodiments in many different forms, herein described in detail preferred embodiments of the invention with the understanding that the present disclosure is to be considered exemplary of the principles of the invention and is not intended to limit the invention to the embodiments described.

A solution of the present invention useful for flushing an intravascular catheter includes a pharmacologically acceptable sodium salt such as sodium chloride or the like in a concentration of between about 820 mg to about 900 mg, a pharmacologically acceptable calcium salt, such as calcium chloride dihydrate or the like in a concentration between about 30.0 mg to about 36.0 mg, a pharmacologically acceptable potassium salt, such as potassium chloride or the like in a concentration between about 28.5 to about 31.5 mg and about one milligram per milliliter polyhexamethylene biguanide hydrochloride in an aqueous admixture with one hundred milliliters of water for injection U.S.P. For particular applications, the solution of the invention may also include sodium lactate in a concentration between about 290 mg and about 330 mg in the one hundred milliliter aqueous admixture.

The solution of the invention is preferably exposed to conditions that substantially render any microorganisms therein non-viable and packaged in a sealed vessel, such as a syringe, septum-closed vial or an ampoule that is substantially resistant to the passage of microorganisms. Preferably, the sealed vessel contains an aliquot of the flush solution that is sufficient to perform one catheter flush procedure. For particular applications, a bulk vessel may be preferred that contains a sufficient amount of the solution to dispense multiple aliquots for individual catheter flush procedures.

An in vitro comparison between the catheter flush solution containing sodium lactate of the invention and a catheter flush solution disclosed in U.S. Pat. No. 5,362,754 including minocycline and ethylene diaamine tetraacetic acid (M-EDTA) was conducted. The results of this evaluation of the two solutions' activity on tubing that had *P. aeruginosa* in established biofilms suprisingly showed that the catheter flush solution of the invention performed similarly to the M-EDTA solution disclosed in U.S. Pat. No. 5,362,754. Table I lists the variables used in the comparison and the results. In this comparison, segments of test tubing were incubated in trypticase soy broth (TSB) containing *P. aeruginosa* to acquire a loading in the tubing bore of the biofilm containing the microorganism. The tubing segments were recovered from the broth and attached to syringes containing the catheter flush solutions. The test solutions were injected into the tubing segments with the syringe and allowed to stand at ambient conditions. At the times indicated, the solutions were withdrawn from the particular segments of tubing, the tubing bore washed with sterile saline and the saline was cultured providing the results in the table. In this comparison, the flush solution of the invention included sodium lactate in the concentration as described above.

TABLE I

| Time elapsed (hours) | Tubing Material | Test solution | Colony forming units (CFU) recovered/cm$^2$ of tubing |
|---|---|---|---|
| 0 | Silicone | None (control) | >9,500 |
| 0 | Polyvinylchloride | None (control) | >15,000 |
| 3 | Silicone | 5,362,754 | >9,500 |
| 3 | Silicone | Invention | >9,500 |
| 3 | Polyvinylchloride | 5,362,754 | <15 |
| 3 | Polyvinylchloride | Invention | <15 |
| 5 | Silicone | 5,362,754 | <9.5 |
| 5 | Silicone | Invention | 9,500 |
| 5 | Polyvinylchloride | 5,362,754 | <15 |
| 5 | Polyvinylchloride | Invention | <15 |
| 24 | Silicone | 5,362,754 | 13 |
| 24 | Silicone | Invention | 9.5 |
| 24 | Polyvinylchloride | 5,362,754 | <15 |
| 24 | Polyvinylchloride | Invention | <15 |

Established biofilms are difficult to eradicate and the bacteria established in these films are resistant to conventional antibiotic treatment. The flush solution of U.S. Pat. No. 5,362,754 has been shown to be effective in preventing device related infections, partially or completely due to its effect on biofilms and the bacteria in these films.

Additionally, a comparison of the minimum inhibitory concentration (MIC) of the solution of the invention after filter sterilization and after steam sterilization following a widely accepted protocol in an autoclave. The flush solutions of the invention showed no difference in the MIC between the filter sterilized by passage of the solution through a 0.22 micron filter and the steam sterilized solution of the invention against *S. aureus*, *P. aeruginosa*, *E. Coli* and *C. albicans*. The stability of the flush solution to steam sterilization suggests that the long term shelf stability at ambient temperatures of prepackaged unit dose aliquots of the solution should be at least two years, although this is yet to be confirmed.

A method for flushing an intravenous catheter includes providing an admixed solution substantially free of microorganisms containing between about 820 mg to about 900 mg of sodium chloride, between about 28.5 to about 31.5 mg of potassium chloride, between about 30.0 to about 36.0 calcium chloride dihydrate, about 100 mg polyhexamethylene biguanide hydrochloride in one hundred milliters of water for injection U.S.P. The solution of the invention preferably includes between about 290 mg to about 330 mg of sodium lactate. The method includes filling a fluid handling device, preferably a syringe, with an aliquot of the solution sufficient to perform a catheter flush procedure. The preferred amount for the flush procedure is generally about two or three milliliters. The practitioner then attaches the syringe to the target intravascular catheter that requires flushing and administers the solution into the catheter, thereby completing the flush procedure. The frequency of the performance of the procedure may be once daily or, for particular situations, more or less frequently.

Toxicity studies of the preferred catheter flush solution of the invention containing sodium lactate show that at doses of the polyhexamethylene biguanide hydrochloride at up to one time, ten times, fifty times and seventy times the expected dose level (two ml flush in a seventy kg. Human) level, there was no significantly greater biological reactivity compared to controls. Toxicity studies of the preferred catheter flush solution at eighty five times (lowest observable acute effect level), one hundred times, and two hundred times the expected dose level, there was slight to moderate biological reactivity compared to controls. At a dosage level of one thousand times the expected dosage level, there was significantly greater reactivity compared to controls.

The pharmacologically acceptable salts used in the preparation of the flush solution of the invention, i.e. sodium chloride, calcium chloride dihydrate, potassium chloride and sodium lactate are widely available. Any source of these materials meeting the requirements of the United States Pharmacopeia (U.S.P.) are satisfactory. The same is true for the water for injection U.S.P. Any water that meets the requirements listed in the U.S.P. for water for injection is satisfactory for use in the invention.

Polyhexamethylene biguanide hydrochloride with a molecular formula of $C_8H_{18}N_5Cl(C_8H_{18}N_5Cl)_n$ is a polymeric material with a molecular weight between about 1800 and about 2400 and is available as a twenty percent aqueous solution from Zeneca, Wilmington, Del. as Cosmocil® CQ. The compound has high activity against a wide range of microorganisms, it has very low mammalian toxicity and is chemically stable. The compound is widely used as a preservative in cleaning solutions for contact lenses. Polyhexamethylene biguanide hydrochloride is also referred to as polyaminopropyl biguanide by the Cosmetic Toiletries and Fragrances Association (CTFA) who recognize its use as a preservative in water in oil and oil in water emulsions and as a antimicrobial agent in surgical scrubs.

The pharmacologically acceptable salts and the water for injection U.S.P. portion of the solution of the invention substantially corresponds to the U.S.P. formulation for Ringer's solution and Lactated Ringer's solution. This portion is well recognized as a benign vehicle for intravenous infusion. The addition of the polyhexamethylene biguanide hydrochloride at the level disclosed herein suprisingly renders the solution substantially as capable of eliminating microorganisms present in established biofilms as the combination of the M-EDTA of the art. Unlike the previous catheter flush solution of the art, the catheter flush solution of the invention exhibits good thermal stability, a property that makes it suitable for packaging in ready-to-use unit dose kits capable of being stored at ambient conditions.

What is claimed is:

1. A solution useful for flushing an intravascular catheter and having activity against microorganisms in established biofilms consisting essentially of:

a pharmacologically acceptable sodium salt, a pharmacologically acceptable calcium salt, a pharmacologically acceptable potassium salt and about one gram per milliliter polyhexamethylene biguanide in aqueous admixture.

2. The catheter flush solution of claim 1 wherein said pharmacologically acceptable sodium salt is sodium chloride, said pharmacologically acceptable calcium salt is calcium chloride and said pharmacologically acceptable potassium salt is potassium chloride.

3. The catheter flush solution of claim 2 wherein said sodium chloride is present in a concentration between about 820 mg to about 900 mg, said potassium chloride is present in a concentration between about 28.5 mg to about 31.5 mg and said calcium chloride is present in a concentration between about 30.0 to about 36.0 mg as the dihydrate in one hundred milliliters of water.

4. The solution of claim 3 further comprising sodium lactate.

5. The solution of claim 4 wherein said sodium lactate is present in a concentration between about 290 mg and about 330 mg in said one hundred milliliters of water for injection U.S.P.

6. The solution of claim 1 being sealed in a package resistant to the passage of microorganisms and exposed to thermal energy sufficient to render any microorganism therein non-viable.

7. The solution of claim 1 being passed through a filter having a pore size sufficient to substantially remove any microorganism present therein and sealed in a suitable package substantially free of and resistant to the passage of microorganisms.

8. A solution useful for flushing an intravascular catheter and having activity against microorganisms in established biofilms consisting essentially of an admixture of sodium chloride in a concentration between about 820 mg to about 900 mg, potassium chloride in a concentration between about 28.5 mg to about 31.5 mg , calcium chloride in a concentration between about 30.0 to about 36.0 mg as the dihydrate and about 100 mg of polyhexamethylene biguanide in one hundred milliliters of water.

9. The solution of claim 8 further comprising said solution being exposed to conditions capable of rendering any microorganisms therein substantially non-viable and wherein aliquots of said solution are sealed in a fluid handling device suitable for administration of said solution into a intravascular catheter disposed in a patient.

10. The solution of claim 8 further comprising sodium lactate in a concentration between about 290 mg and about 330 mg in said aqueous admixture.

* * * * *